US008765256B2

(12) United States Patent
Ohrlander et al.

(10) Patent No.: US 8,765,256 B2
(45) Date of Patent: *Jul. 1, 2014

(54) SUBSTRATE HAVING AN ELECTRON DONATING SURFACE WITH METAL PARTICLES COMPRISING PALLADIUM ON SAID SURFACE

(71) Applicant: Bactiguard AB, Stockholm (SE)

(72) Inventors: Mattias Ohrlander, Enskede (SE); Billy Södervall, Markaryd (SE)

(73) Assignee: Bactiguard AB (SE)

( * ) Notice: Subject to any disclaimer, the term of this patent is extended or adjusted under 35 U.S.C. 154(b) by 0 days.

This patent is subject to a terminal disclaimer.

(21) Appl. No.: 13/674,893

(22) Filed: Nov. 12, 2012

(65) Prior Publication Data

US 2013/0115262 A1 May 9, 2013

Related U.S. Application Data

(63) Continuation of application No. 12/296,429, filed as application No. PCT/SE2007/050226 on Apr. 5, 2007, now Pat. No. 8,309,216.

(60) Provisional application No. 60/790,307, filed on Apr. 7, 2006.

(51) Int. Cl.
*B32B 5/16* (2006.01)
*B05D 1/12* (2006.01)

(52) U.S. Cl.
USPC .......................... 428/328; 428/451; 427/180

(58) Field of Classification Search
USPC .................................. 428/328, 451; 427/180
See application file for complete search history.

(56) References Cited

U.S. PATENT DOCUMENTS

| | | | |
|---|---|---|---|
| 4,795,475 A | 1/1989 | Walker | |
| 5,320,908 A * | 6/1994 | Sodervall et al. | 428/461 |
| 5,395,651 A | 3/1995 | Sodervall et al. | |
| 5,695,857 A | 12/1997 | Burrell et al. | |
| 5,747,178 A | 5/1998 | Sodervall et al. | |
| 5,753,251 A | 5/1998 | Burrell et al. | |
| 5,935,719 A | 8/1999 | Abbott | |
| 5,965,204 A | 10/1999 | Sodervall et al. | |
| 6,080,490 A | 6/2000 | Burrell et al. | |
| 6,168,633 B1 | 1/2001 | Shoher et al. | |
| 6,224,983 B1 | 5/2001 | Sodervall et al. | |
| 6,284,387 B1 | 9/2001 | Nakao | |
| 6,399,039 B2 | 6/2002 | Ostgard | |
| 6,716,895 B1 | 4/2004 | Terry | |
| 6,831,024 B2 | 12/2004 | Kim | |
| 7,195,615 B2 | 3/2007 | Tan | |
| 8,309,216 B2 | 11/2012 | Ohrlander et al. | |
| 2001/0005499 A1 | 6/2001 | Ostgard | |
| 2003/0102225 A1 | 6/2003 | Kim | |
| 2004/0121077 A1 | 6/2004 | Park et al. | |
| 2005/0159306 A1 | 7/2005 | Kezuka et al. | |
| 2006/0003019 A1 | 1/2006 | Moller et al. | |
| 2006/0251874 A1 | 11/2006 | McClure et al. | |
| 2007/0237945 A1 | 10/2007 | Ohrlander et al. | |
| 2007/0237946 A1 | 10/2007 | Ohrlander et al. | |

FOREIGN PATENT DOCUMENTS

| | | |
|---|---|---|
| CA | 2016081 C | 4/1999 |
| CH | 654738 A5 * | 3/1986 |
| EP | 0400349 A1 | 12/1990 |
| EP | 0693576 A1 | 1/1996 |
| EP | 0937398 A1 | 8/1999 |
| EP | 1375700 A1 | 1/2004 |
| JP | 63-200752 A | 8/1988 |
| JP | 11-302570 A | 11/1999 |
| JP | 2001-234392 A | 6/2001 |
| WO | 2002/017984 A1 | 3/2002 |
| WO | 2003/063925 A1 | 8/2003 |
| WO | 2003/076341 A2 | 9/2003 |
| WO | 2004/045577 A1 | 6/2004 |
| WO | 2005/072281 A2 | 8/2005 |
| WO | 2005/073289 A1 | 8/2005 |
| WO | WO 2005073289 A1 * | 8/2005 |
| WO | 2005/072281 A3 | 11/2005 |

OTHER PUBLICATIONS

Final Office Action received for U.S. Appl. No. 11/784,332, mailed on Jul. 27, 2011, 12 pages.
Non Final Office Action received for U.S. Appl. No. 11/784,332, mailed on Aug. 4, 2010, 12 pages.
Non Final Office Action received for U.S. Appl. No. 11/784,332, mailed on Feb. 19, 2010, 22 pages.
Non Final Officce Action received for U.S. Appl. No. 11/784,332, mailed on Jan. 24, 2012, 7 pages.
Non-Final Office Action received for U.S. Appl. No. 11/784,332, mailed on Dec. 23, 2010, 12 pages.
Final Office Action received for U.S. Appl. No. 11/784,558, mailed on Dec. 8, 2010, 17 pages.
Non Final Office Action received for U.S. Appl. No. 11/748,558, mailed on Mar. 24, 2010, 18 pages.
Final Office Action received for U.S. Appl. No. 12/296,429, mailed on Mar. 9, 2012, 15 pages.
Non Final Office Action received for U.S. Appl. No. 12/296,429, mailed on Jul. 12, 2011, 25 pages.
Notice of Allowance received for U.S. Appl. No. 12/296,429, mailed on Jul. 5, 2012, 12 pages.
Non Final Office Action Received for U.S. Appl. No. 13/155,334, mailed on May 22, 2012, 33 pages.
Gabriel et al., "Effects of Silver on Adherence of Bacteria to Urinary Catheters: In Vitro Studies", Current Microbiology, vol. 30, 1995, pp. 17-22.

(Continued)

*Primary Examiner* — Michael Bernshteyn
(74) *Attorney, Agent, or Firm* — Hiscock & Barclay, LLP

(57) ABSTRACT

A substrate is provided with a metal electron donating surface made up of metal particles on the substrate, the metal particles having palladium and at least one metal selected from gold, ruthenium, rhodium, osmium, iridium, or platinum. The amount of the metal particles present on the substrate is from about 0.001 to about 8 μg/cm² and wherein the substrate is part of a device or object from aspects of the medical field.

66 Claims, No Drawings

(56) References Cited

OTHER PUBLICATIONS

Moller et al., "A New Approach for Biologically-Inhibiting Surfaces", Journal of Applied Surface Finishing, vol. 2, No. 2, 2007, pp. 149-157.

Saygan et al., "Gold and Gold-Palladium Coated Polypropylene Grafts in a S. Epidermidis Wound Infection Model", Journal of Surgical Research, vol. 131, 2006, pp. 73-79.

International Search Report received for PCT Patent Application No. PCT/SE2006/050485, mailed on Mar. 1, 2007, 5 pages.

International Search Report received for PCT Patent Application No. PCT/SE2007/050225, mailed on Jul. 4, 2007, 6 pages.

International Search Report received for PCT Application No. PCT/SE2007/050226, mailed on Jul. 4, 2007, 6 pages.

Sodervall et al., Unpublished U.S. Appl. No. 07/630,333, filed Dec. 13, 1900, titled "Deposition of Silver Layer on Nonconducting Substrate".

Sodervall et al., Unpublished U.S. Appl. No. 07/347,016, filed May 4, 1989, titled "Deposition of Silver Layer on Nonconducting Substrate".

Final Office Action received for U.S. Appl. No. 11/784,332, mailed on Oct. 2, 2012, 14 pages.

Extended European Search Report received for European Patent Application No. 07748386.5, mailed on Aug. 2, 2012, 5 pages.

Notice of Allowance received for U.S. Appl. No. 13/155,334, mailed on Nov. 26, 2012, 10 pages.

\* cited by examiner

SUBSTRATE HAVING AN ELECTRON DONATING SURFACE WITH METAL PARTICLES COMPRISING PALLADIUM ON SAID SURFACE

CROSS REFERENCE TO RELATED APPLICATIONS

This application is a Continuation of U.S. patent application Ser. No. 12/296,429 (Now U.S. Pat. No. 8,309,216), filed Dec. 5, 2008, which is the National Stage of International Patent Application of PCT/SE2007/050226, filed Apr. 5, 2007, which claims the benefit of U.S. Provisional Patent Application Ser. No. 60/790,307, filed Apr. 7, 2006, each of which is hereby incorporated by reference in its entirety.

FIELD OF THE INVENTION

The present invention relates to a new substrate with nano particles, which makes it possible to modify surface properties relating to biocompatibility as well as antimicrobial properties in a repeatable and controlled manner. Examples of surface properties, which can be modified, include but are not limited to hydrophobicity, protein adsorption, adhesion of bacteria, tissue ingrowth, complement activation, inflammatory response, thrombogenicity, friction coefficient, and surface hardness. Examples of uses of the substrate include but are not limited to preventing transmission of bacteria and in particular nosocomial infections. The present invention further relates to objects comprising said new substrate. The present invention further relates to the use of said substrate. Finally the present invention further relates to a method for the manufacture of such a substrate.

BACKGROUND

It has always been desirable to modify surface characteristics to achieve useful properties. In particular it is desired to be able to modify surface properties that are important in connection with antimicrobial and biocompatible objects. Examples of known surface modifications for different purposes are outlined below.

U.S. Pat. No. 6,224,983 discloses an article with an adhesive, antimicrobial and biocompatible coating comprising a layer of silver stabilised by exposure to one or more salts of one or more metals selected from the group consisting of platinum, palladium, rhodium, iridium, ruthenium and osmium. The thickness of the silver layer is in the range 2-2000 Å (Ångström, Angstrom, $10^{-10}$ m) and further disclosed ranges are 2-350 Å and 2-50 Å. There are also examples of a thickness of the silver layer of 50 Å, 350 Å, 500 Å, and 1200 Å. The substrate may be latex, polystyrene, polyester, polyvinylchloride, polyurethane, ABS polymers, polycarbonate, polyamide, polytetrafluoroethylene, polyimide or synthetic rubber.

U.S. Pat. No. 5,965,204 discloses a method for preparing an article made of a nonconducting substrate having a coating comprising a silver layer, which has been deposited after activating the surface with stannous ions. There is also disclosed a coating further comprising a platinum group metal or gold. The thickness of the silver layer is in the range 2-2000 Å and further disclosed ranges are 2-350 Å and 2-50 Å. There are also examples of a thickness of the silver layer of 50 Å, 350 Å, 500 Å, and 1200 Å.

U.S. Pat. No. 5,747,178 discloses an article made by depositing a silver layer. The layer is said to be adhesive, antimicrobial and biocompatible. The silver layer may be stabilized by exposure to a salt solution of one or more platinum group metals or gold. The thickness of the silver layer is in the range 2-2000 Å and further disclosed ranges are 2-350 Å and 2-50 Å. There are also examples of a thickness of the silver layer of 50 Å, 350 Å, 500 Å, and 1200 Å. The article may be made of latex, polystyrene, polyester, polyvinylchloride, polyurethane, ABS polymers, polycarbonate, polyamide, polytetrafluoroethylene, polyimide or synthetic rubber.

U.S. Pat. No. 5,395,651 discloses a method of preparing an antimicrobial device comprising a nonconducting material with a silver coating. The coating also comprises a platinum group metal and/or gold. The method comprises the steps: 1 activating the surface to be coated; 2 depositing silver on the surface; 3 treating the surface with a salt of a platinum group metal and/or gold, which is to be carried out for only sufficient time to result in a thin coating; 4 rinsing with water. The treatment of step 3 can utilise a salt of platinum or palladium in combination with gold. Nothing is said about the thickness of the coating of the platinum group metal and/or gold. The coating is only described as a thin coating. Nothing is said about metal particles on the silver coating. The thickness of the silver layer is in the range 2-2000 Å and further disclosed ranges are 2-350 Å and 2-50 Å. There are also examples of a thickness of the silver layer of 50 Å, 350 Å, 500 Å, and 1200 Å.

U.S. Pat. No. 5,320,908 discloses an adhesive, antimicrobial, and biocompatible coating consisting essentially of a layer of silver overlaid by one or more platinum group metals or gold. The coating may be transparent to the human eye. The thickness of the silver layer is in the range 2-2000 Å and further disclosed ranges are 2-350 Å and 2-50 Å. There are also examples of a thickness of the silver layer of 50 Å, 350 Å, 500 Å, and 1200 Å. The article may be made of latex, polystyrene, polyester, polyvinylchloride, polyurethane, ABS polymers, polycarbonate, polyamide, polytetrafluoroethylene, polyimide or synthetic rubber.

U.S. Pat. No. 5,695,857 discloses antimicrobial surfaces with several layers of one first metal and a second nobler metal. The antimicrobial active metal may for instance be platinum, gold, silver, zinc, tin, antimony and bismuth. The nobler metal may for instance be selected from the group consisting of platinum, osmium, iridium, palladium, gold, silver and carbon. The surface is to be used with biological fluids and each of the layers not in contact with the substrate are discontinuous so that the layer below is exposed. One example of a surface is silver coated with gold or platinum. Other examples are copper in combination with silver, copper in combination with a copper silver alloy, copper in combination with gold or a silver copper alloy in combination with gold.

CH 654 738 A5 discloses surgical implants made of stainless steel, which is coated with a first layer of copper and a second layer of silver, gold, rhodium or palladium. Silver is described to have a bactericidic action. CH 654 738 A5 explicitly discloses a surface where stainless steel is coated with 10 μm copper and 5 μm (50 000 Å) palladium. All surfaces disclosed in CH 654 738 A5 have a layer of 10 μm copper (100 000 Å) and either 10 μm silver or 5 μm gold or 5 μm palladium.

WO 2005/073289 discloses fibres made of a polymer composite comprising metal nanoparticles. It is stated that many metals have antimicrobial effects. Antimicrobial fibres are mentioned. One example is a hydrophilic fibre used in antimicrobial would dressings. Fibres with antimicrobial properties can comprise Ag, Au, Pt, Pd, Ir, Sn, Cu, Sb, Bi or Zn or any combination thereof.

SHORT SUMMARY OF THE PRESENT INVENTION

A problem in the state of the art regarding surfaces is how to provide a surface which for example is antimicrobial and biocompatible, wherein it in a repeatable way is possible to modify the hydrophobicity, protein adsorption, adhesion of bacteria, tissue ingrowth, complement activation, inflammatory response, thrombogenicity, friction coefficient, and surface hardness.

The present inventors have discovered that the above-mentioned problem in the state of the art is solved by a substrate having an electron donating surface, characterized in that there are metal particles on said surface, said metal particles comprise palladium and at least one metal selected from the group consisting of gold, ruthenium, rhodium, osmium, iridium, and platinum and wherein the amount of said metal particles is from about 0.001 to about 8 $\mu g/cm^2$. Further embodiments of the present invention are defined in the appended dependent claims, which hereby are incorporated by reference.

DESCRIPTION

Definitions

Before the invention is disclosed and described in detail, it is to be understood that this invention is not limited to particular configurations, process steps and materials disclosed herein as such configurations, process steps and materials may vary somewhat. It is also to be understood that the terminology employed herein is used for the purpose of describing particular embodiments only and is not intended to be limiting since the scope of the present invention is limited only by the appended claims and equivalents thereof.

It must be noted that, as used in this specification and the appended claims, the singular forms "a", "an" and "the" include plural referents unless the context clearly dictates otherwise.

The following terms are used throughout the description and the claims.

"Adhesion of bacteria" as used herein is the phenomenon where bacteria adhere to a surface.

"Antimicrobial" as used herein is the property of suppressing or eliminating microbial growth.

"Biocompatible" as used herein is the ability of a material to perform with an appropriate host response in a specific application.

"Biofilm" as used herein is a thin layer in which microorganisms are embedded. Biofilms occur when microorganisms colonise a surface.

"Complement activation" as used herein is a complex system of factors in blood plasma that may be activated by a chain reaction from component C1 to C9, which give rise to a number of biological effects. Complement activation occurs in two ways a) the classical C1 to C9, or b) the alternative by direct activation of C3.

"Contact angle". For a given droplet on a solid surface the contact angle is a measurement of the angle formed between the surface of a solid and the line tangent to the droplet radius from the point of contact with the solid.

"Electron donating material" as used herein is a material, which in connection with another more noble material has the ability to transfer electrons to the more noble material. An example is a less noble metal together with a more noble metal.

"Electron donating surface" as used herein is a surface layer comprising an electron donating material.

"Hydrophobicity" of a surface as used herein describes the interactions between the surface and water. Hydrophobic surfaces have little or no tendency to adsorb water and water tends to "bead" on their surfaces. The term hydrophobicity of a surface is also closely linked with its surface energy. Whereas surface energy describes interactions of the surface with all molecules, the hydrophobicity describes the interactions of the surface with water.

"Hysteresis of contact angle" as used herein is the difference between the advancing and receding contact angle values. The advancing contact angle of a drop of water on a surface is the contact angle when the boundary between water and air is moving over and wetting the surface, while the receding angle is the contact angle when boundary between water and air is withdrawn over a pre-wetted surface.

"Inflammatory response" occurs when tissues are injured by viruses, bacteria, trauma, chemicals, heat, cold or any other harmful stimulus. Chemicals including bradykinin, histamine, serotonin and others are released by specialised cells. These chemicals attract tissue macrophages and white blood cells to localise in an area to engulf and destroy foreign substances.

"Modify" either means reducing or enhancing a property.

"Noble" is used herein in a relative sense. It is used to relate materials including metals to each other depending on how they interact with each other. When two metals are submerged in an electrolyte, while electrically connected, the term "less noble" metal is used to denote the metal which experiences galvanic corrosion. The term "more noble" is used to denote the other metal. Electrons will be transferred from the "less noble" metal to the more noble metal.

"Nosocomial infection" as used herein describes an infectious disease spreading in a hospital environment.

"Protein adsorption" as used herein is the phenomenon where proteins adhere to a surface due to overall attractive forces between the proteins and the surface.

"Substrate" as used herein is the base, which is treated according to the present invention.

"Tissue ingrowth" is the process where cells start to grow on a surface, forming new tissue.

"Thrombogenicity" as used herein is the ability of a substrate to induce clotting of blood.

DETAILED DESCRIPTION OF THE PRESENT INVENTION

According to the present invention a substrate is treated to give it desired properties. The substrate can be made of a wide range of materials. In one embodiment the substrate is made of a material, which has an electron-donating surface. In an alternative embodiment it is made of a material, which does not have an electron-donating surface. In the case of an electron-donating surface the metal particles can be applied directly on to the electron-donating surface. In the case where the surface it not electron donating, a layer of an electron donating material has to be applied to create an electron donating surface.

The present invention comprises a substrate having an electron donating surface, characterized in that there are metal particles on said surface, said metal particles comprise palladium and at least one metal selected from the group consisting of gold, ruthenium, rhodium, osmium, iridium, and platinum and wherein the amount of said metal particles is from about 0.001 to about 8 $\mu g/cm^2$. A preferred amount of said metal particles is from about 0.01 to about 4 $\mu g/cm^2$. A particularly preferred amount of said metal particles is from about 0.01 to about 1 µg/cm². Examples of ranges within from about 0.001 to about 8 µg/cm² include 0.001-6, 0.001-4, 0.001-2, 0.001-1, 0.001-0.5, 0.001-0.25, 0.001-0.15, 0.15-8, 0.25-8, 0.5-8, 1-8, 2-8, 4-8, 6-8, 0.15-0.25, 0.25-0.5, 0.5-1, 1-2, 2-4, 4-6 1-3, and 3-6 µg/cm².

Either the substrate itself is electron donating or there is applied a layer of an electron donating material on the substrate. In the case where the electron donating material is applied on the substrate it is applied in an amount of from about 0.05 to about 12 µg/cm². The amount of the substrate can also be within other ranges as long as the amount is from about 0.05 to about 12 µg/cm². Examples of such other ranges include 0.05-10, 0.05-8, 0.05-6, 0.05-4, 0.05-2, 0.05-1, 0.05-0.5, 0.05-0.25, 0.05-0.15, 0.15-12, 0.25-12, 0.5-12, 1-12, 2-12, 4-12, 6-12, 8-12, 10-12, 0.15-0.25, 0.25-0.5, 0.5-1, 1-2, 2-4, 4-6, 6-8, 8-10, 1-5, and 5-10 µg/cm².

An electron donating material does not necessarily have an electron-donating surface. An example is aluminium, which in air gets an oxide layer, which is not an electron-donating surface.

The electron donating material is any material with the ability to form an electron-donating surface, such as a conducting polymer or a metal. In the case of a metal it must be less noble than any of the metals in the group consisting of palladium, gold, ruthenium, rhodium, osmium, iridium, and platinum.

A preferred metal for use as an electron-donating surface is a metal selected from the group consisting of silver, copper and zinc.

In one embodiment of the present invention the substrate is a polymeric substrate.

In one embodiment the substrate is selected from the group consisting of latex, vinyl, polymers comprising vinyl groups, polyurethane urea, silicone, polyvinylchloride, polypropylene, styrene, polyurethane, polyester, copolymerisates of ethylene vinyl acetate, polystyrene, polycarbonate, polyethylene, polyacrylate, polymethacrylate, acrylonitrile butadiene styrene, polyamide, and polyimide, or mixtures thereof.

In another embodiment of the present invention the substrate is selected from the group consisting of a natural polymer, a degradable polymer, an edible polymer, a biodegradable polymer, an environmental friendly polymer, and a medical grade polymer.

In another embodiment of the present invention the substrate is a metal.

A preferred metal for the substrate is selected from the group consisting of stainless steel, medical grade steel, titanium, medical grade titanium, cobalt, chromium and aluminium or mixtures thereof.

In another embodiment of the present invention the substrate is selected from the group consisting of glass, minerals, zeolites, stone and ceramics.

In another embodiment of the present invention the substrate is selected from the group consisting of paper, wood, woven fibres, fibres, cellulose fibres, leather, carbon, carbon fibres, graphite, polytetrafluoroethylene, and polyparaphenyleneterephthalamide.

In another embodiment of the present invention the substrate has the shape of a particle.

In one embodiment of the present invention there is provided an object comprising a substrate according to the present invention. Examples of objects comprising a substrate according to the present invention include medical devices, medical instruments, disposable articles, medical disposable articles. Further examples of objects comprising a substrate coated according to the present invention include contact lenses, pacemakers, pacemaker electrodes, stents (bare metal and drug eluting), dental implants, rupture nets, rupture mesh, blood centrifuge equipment (in contact with blood), surgical instruments, gloves, blood bags, artificial heart valves, central venous catheters, peripheral venous catheters, vascular ports, haemodialysis equipment, peritoneal dialysis equipment, plasmapheresis devices, inhalation drug delivery devices, vascular grafts, arterial grafts, cardiac assist devices, wound dressings, intermittent catheters, ECG electrodes, peripheral stents, bone replacing implants, orthopaedic implants, orthopaedic devices (screws, pins, staples, suture anchors etc.), tissue replacing implants, intraocular lenses, sutures, needles, drug delivery devices, endotracheal tubes, shunts, drains, suction devices, hearing aid devices, urethral medical devices, and artificial blood vessels.

The particles must always comprise palladium. In addition to palladium there is at least one other metal. A ratio of palladium to other metals in the metal particles of from about 0.01:99.99 to about 99.99:0.01 can be used in the present invention. A ratio from about 0.5:99.5 to about 99.8:0.2 is preferred. Particularly preferred ratios are from about 2:98 to about 95:5. Very particularly preferred ratios are 5:95 to 95:5. In another embodiment the ratios are from about 10:90 to about 90:10. A person skilled in the art realises that the ration also can be in other intervals. Examples of other ranges for the ratio include: 0.01:99.99 to 0.05:99.95, 0.05:99.95 to 0.1:99.9, 0.1:99.9 to 0.5:99.5, 0.5:99.5 to 1:99, 1:99 to 2:98, 2:98 to 4:96, 4:96 to 6:94, 6:94 to 8:92, 8:92 to 10:90, 10:90 to 20:80, 20:80 to 30:70, 30:70 to 40:60, 40:60 to 50:50, 50:50 to 60:40, 60:40 to 70:30, 70:30 to 80:20, 80:20 to 90:10, 90:10 to 92:8, 92:8 to 94:6, 94:6 to 96:4, 96:4 to 98:2, 98:2 to 99:1, 99:1 to 99.5:0.5, 99.5:0.5 to 99.9:0.1 to 99.95:0.05, 99.95:0.05 to 99.99:0.01

In one embodiment of the present invention said metal particles, in addition to palladium, comprise gold.

The present inventors have discovered that advantageous properties are achieved when said metal particles have an average size of from about 10 to about 10000 Å.

In one embodiment the average sizes for said metal particles are from about 100 to about 600 Å.

A person skilled in the art realises that the particle size can be in different intervals within from about 10 to about 10000 Å. Examples of such intervals include 10-8000 Å, 10-6000 Å, 10-4000 Å, 10-2000 Å, 10-1000 Å, 10-100 Å, 100-10000 Å, 1000-10000 Å, 2000-10000 Å, 4000-10000 Å, 6000-10000 Å, 8000-10000 Å, 100-1000 Å, 1000-2000 Å, 2000-4000 Å, 4000-6000 Å, 6000-8000 Å, 1000-5000 Å, and 5000-8000 Å.

In another aspect of the present invention there is provided an object comprising any of the substrates described herein.

There is also provided a medical device comprising any of the substrates described herein.

A disposable article comprising any of the substrates described herein is also provided.

The present invention also provides a dental article, as well as dental equipment, dental implants, and dental devices, comprising any of the substrates described herein.

The applied amount of the metal particles is expressed in µg/cm² and it must be realised that the metal particles do not form a covering layer, but instead are uniformly distributed particles or clusters on said electron donating surface.

An applied layer of an electron donating material is preferably applied so that it is uniform, essentially without agglomerates or clusters on the surface. If the electron donating surface layer is homogenous and uniform the applied amount in µg/cm² may be converted to a thickness in Å. An applied amount of 0.05-4 µg/cm² corresponds to about 4.8-

380 Å, 0.5-8 µg/cm² corresponds to about 48-760 Å, and 0.8-12 µg/cm² corresponds to about 76-1140 Å.

In one embodiment of the present invention the electron-donating surface is a layer of commercially available essentially pure silver, which does not exclude the possibility of small amounts of impurities.

If the substrate does not have an electron donating surface and thus a deposition of an electron donating surface layer is necessary, the deposition is performed using a method selected from the group consisting of chemical vapour deposition, sputtering, and deposition of metal from a solution comprising a metal salt. A uniform layer essentially without clusters or agglomerates is the result of the deposition. Preferably the deposition is carried out so that the first layer has good adhesion to the substrate.

Now there is described one embodiment of the present invention for preparation of the coated substrate. For substrates which do not have an electron donating surface the method includes some or all of the following steps:
1. pre-treatment
2. rinsing
3. activation
4. deposition of an electron donating surface
5. rinsing
6. deposition of metal particles
7. rinsing
8. drying For objects with an electron-donating surface the method comprises the steps
1. rinsing
2. deposition of metal particles
3. rinsing
4. drying In the following, one embodiment of steps 1 to 9 for substrates which do not have an electron-donating surface is described more in detail.

The pre-treatment can be made in an aqueous solution of a stannous salt containing 0.0005 to 30 g/l of stannous ions. The pH is 1 to 4 and adjusted by hydrochloric and/or sulphuric acid. The treatment time is 2-60 minutes at room temperature. After the pre-treatment the surface is rinsed in demineralised water, but not dried.

The activated and rinsed substrate is transferred to the deposition solution. The deposition solution has a pH of not less than 8. It includes a metal salt selected from the group consisting of a silver salt, a zinc salt, and a copper salt. In one embodiment of the present invention the salt is silver nitrate ($AgNO_3$). The metal salt is used in an effective amount of no more than about 0.10 grams per liter, preferably about 0.015 grams per liter. If the metal content is above about 0.10 grams per liter, the elemental metal may form nonuniformly, in the solution or on the container walls. If the metal content is below an effective amount, there is insufficient metal to form a film in the desired time.

A second component of the deposition solution is a reduction agent that reduces the metal-containing salt to elemental metal. The reduction agent must be present in an amount sufficient to accomplish the chemical reduction. Acceptable reduction agents include formaldehyde, hydrazine sulphate, hydrazine hydroxide, and hypo phosphoric acid. In one embodiment of the present invention it is present in an amount of about 0.001 milliliters per liter of solution. Too large a concentration of the reduction agent causes deposition of metal throughout the solution and on the container walls, while too small a concentration may result in an insufficient formation of metal on the substrate. A person skilled in the art can in the light of this description by routine experimentation determine the desired amount of reduction agent.

Another component of the deposition solution is a deposition control agent that is present in an amount sufficient to slow the deposition reaction to prevent the reduced metal from precipitating directly from solution as a fine metallic powder, or precipitating onto the walls of the container. Operable deposition control agents include inverted sugar, also known as invertose, succinic acid, sodium citrate, sodium acetate, sodium hydroxide, potassium hydroxide, sodium tartrate, potassium tartrate, and ammonia. The deposition control agent is preferably present in an amount of about 0.05 grams per liter of solution. If too little is present, there may occur precipitation of metal clusters instead of a uniform metallic surface. If too much is present, the metal-containing salt may become too stable for the desired precipitation onto the substrate of interest.

The concentrations of the reduction agent and the deposition control agent are adjusted as necessary to achieve the desired results, depending upon the substrate material, the thickness of the film desired, the conditions of deposition, and the concentration of metal in the solution. For example, for thin films the metal salt concentration will be relatively low, as will the concentrations of the reduction agent and the deposition control agent. A person skilled in the art can in the light of this description by routine experimentation determine the desired amount of deposition control agent.

In preparing the deposition solution, each of the components of the solution are preferably individually dissolved in demineralised water. The various pre-solutions are then mixed, and diluted where necessary, in the correct amounts to achieve the concentrations mentioned above.

The combination of a metal salt and reduction agent permits the metal to be reduced from the salt in a suitable state to be deposited upon the surface of the substrate. This method is particularly beneficial to achieve good adhesion of the completed metal film to the substrate surface. Good adhesion is important in nearly all uses.

The substrate surface is exposed to the deposition solution by any appropriate procedure. Dipping into the solution is normally preferred, but the solution may be applied by any convenient technique such as spraying or brushing. The metal film deposits uniformly from the solution at a rate that may be controlled by the concentration of the metal salt. If a thin film is required, the temperature of deposition is maintained sufficiently low so that deposition is controllably slow.

Other methods of applying a metal layer that acts as an electron-donating surface can also be applied in the present invention. Other ways of achieving an electron-donating surface are chemical vapour deposition and sputtering.

After the above-described metal deposition the substrate has an electron-donating surface consisting of a metal. This metal deposition is only necessary if the substrate does not have an electron-donating surface from the start. If the substrate already possesses an electron-donating surface, metal particles can be deposited on the surface without the extra addition of a metal layer. In the latter case the substrate is cleaned thoroughly before application of the particles.

The next step in the manufacturing method is deposition of metal particles.

In one embodiment colloidal suspensions of metals are used to obtain particles comprising palladium and at least another metal on the surface. The metal particles are deposited from a suspension of the desired particles. The composition of the metal particles in the suspension is adjusted according to the preferred value. The substrate with the electron-donating surface is dipped in the suspension of metal particles for a period of time from about a few seconds to about a few minutes or longer.

The suspension of metal particles can be manufactured in several ways. In one embodiment the suspension of metal particles is made from an aqueous solution of a metal salt which is reduced under conditions such that metal particles of a desired size are formed. Mixing a suitable amount of metal salt, reducing agent and stabilising agent achieves this. The same reducing agents and stabilising agents as described above can be used when making the particle suspension. A person skilled in the art can in the light of this description by routine experimentation determine the desired amount of reducing agent and stabilising agent to get the desired particle size. In an alternative embodiment a commercially available colloidal suspension of metal particles is used. Metal particles of the desired composition are used to make the suspension.

In one embodiment the suspension of metal particles is made by diluting with demineralised water a commercially available concentrated colloidal solution of metal particles comprising palladium and at least one metal selected from the group consisting of gold, ruthenium, rhodium, osmium, iridium, and platinum. The substrate is treated with the suspension for a period of time from about a few seconds to about a few minutes or longer. After the treatment the substrate is rinsed in a solvent or water such as demineralised water and left to dry in room temperature.

In one particular non-limiting embodiment the commercially available metal particles consist of 75% palladium and 25% gold.

Thus according to the present invention, a substrate with a particular desired surface can be obtained. For example, one can prepare a substrate having a silver electron donating surface with particles consisting of 75% palladium and 25% gold, or a copper electron donating surface with particles consisting of 85% palladium and 15% ruthenium.

One of the advantages offered by the flexible yet controlled and repeatable method for producing such substrates is that a wide variety of substrates can be produced. As described further herein, certain substrates have improved properties over existing substrates. For example a particular substrate according to the present invention can produce surprising and advantageous modifications of the hydrophobicity of a substrate to which is it applied. Other properties that can be modified in this way by substrates according to claim 1 include protein adsorption, adhesion of bacteria, tissue ingrowth, complement activation, inflammatory response, thrombogenicity, friction coefficient, and surface hardness.

That is, it is possible to adjust the particle size, the composition of the particles and the amount of particles to modify the surface properties of objects to which the substrate is applied.

The present inventors have discovered that it is possible to achieve this by using a substrate according to claim 1. In particular it is possible to adjust the particle size, the composition of particles, and the amount of particles to modify the surface properties.

Substrates according to the present invention can be used for many purposes. They are suitable for use in any application where it is desired to modify hydrophobicity, protein adsorption, adhesion of bacteria, tissue ingrowth, complement activation, inflammatory response, thrombogenicity, friction coefficient, and surface hardness of a substrate.

Properties of the substrate can be both reduced or increased. Thus objects are provided which display at least one area which enhances a feature, and at least one area which reduces a feature. An example is an object with an area that reduces protein adsorption and an area that enhances protein adsorption. Another example is an object with an area that reduces tissue ingrowth and an area that enhances tissue ingrowth.

A substrate according to the present invention also comprises a substrate having an electron donating surface, with metal particles on said surface, said metal particles comprise palladium wherein the amount of said metal particles is from about 0.001 to about 8 $\mu g/cm^2$.

The present invention provides use of a substrate according to the present invention for modifying the protein adsorption to an object comprising said substrate.

The present invention provides use of a substrate according to the present invention for modifying the bacterial adhesion to an object comprising said substrate.

The present invention provides use of a substrate according to the present invention for modifying the tissue ingrowth on an object comprising said substrate.

The present invention provides use of a substrate according to the present invention for modifying the complement activation caused by an object comprising said substrate.

The present invention provides use of a substrate according to the present invention for modifying the inflammatory response caused by an object comprising said substrate.

The present invention provides use of a substrate according to the present invention for modifying the blood clotting caused by an object comprising said substrate.

The present invention provides use of a substrate according to the present invention for preventing bacterial growth.

The present invention provides use of a substrate according to the present invention for preventing transmission of bacteria. Transmission of bacterial infections is prevented by the prevention of the transmission of bacteria. Examples of objects used in this context are handles, buttons, switches, hospital equipment, surgical instruments, medical instruments, kitchen equipment, and all other objects, which are able to transmit bacteria.

The present invention provides use of a substrate according to the present invention for preventing transmission of a nosocomial infection. An object comprising a substrate according to the present invention can be used in any context where it is desired to prevent transmission of a bacterial infection. Preventing transmission of bacteria and thus bacterial infections will in particular prevent nosocomial infections.

Another advantage of the substrate according to the appended claims is that it provides a possibility to modify the friction coefficient. Thus there is provided the use of a substrate according to the present invention for the modification of the friction coefficient of an object comprising said substrate.

Other features of the invention and their associated advantages will be evident to a person skilled in the art upon reading the description and the examples.

It is to be understood that this invention is not limited to the particular embodiments shown here. The following examples are provided for illustrative purposes and are not intended to limit the scope of the invention since the scope of the present invention is limited only by the appended claims and equivalents thereof.

EXAMPLES

Example 1

Hydrophobicity of the Surface as a Function of the Amount of Metal Particles

A uniform layer of silver was deposited on a glass substrate according to the following method. The substrate was immersed in a cleaning solution of chromic acid for 5 minutes at 58° C., followed by rinsing in demineralised water. The surface of the substrate was activated by immersion in a solution of aqueous stannous chloride and then rinsed in demineralised water. The surface of the substrate was then plated with a uniform layer of silver by immersion in 3 deposition solutions comprising silver ions. This yielded a silver surface with an applied amount of 1.2 µg/cm$^2$ corresponding to a thickness of about 115 Å. Particles consisting of 23% palladium and 77% gold were subsequently deposited on the first silver surface by immersion in a dilute suspension comprising metal particles of gold/palladium. The suspension of metal particles was made by reducing a gold salt and a palladium salt with a reducing agent and stabilising the suspension with a stabilising agent. The substrate was subsequently rinsed in demineralised water and dried.

Substrates with different amounts of deposited particles were made using the method outlined above. Amounts of particles were 0, 0.02, 0.11, 0.15, and 0.19 µg/cm$^2$ respectively. For the sample with 0 µg/cm$^2$ no particles were deposited on the surface and hence it consists of a silver surface.

The static contact angle of a drop of water in equilibrium on the different substrates was measured. The advancing and receding contact angles were measured using the Wilhelmy technique.

The difference between the advancing and receding contact angle values is called the contact angle hysteresis and was calculated for the measurements. The result of the experiment is depicted in Table 1.

TABLE 1

| Amount of particles (µg/cm$^2$) | Static contact angle (degrees) | Contact angle hysteresis (degrees) |
| --- | --- | --- |
| 0 | 52 | 70 |
| 0.02 | 50 | 77 |
| 0.11 | 56 | 75 |
| 0.15 | 62 | 80 |
| 0.19 | 62 | 84 |

The surface hydrophobicity of the substrate is thus modified while the surface displays several other useful properties, such as antimicrobial properties, inherent of the substrates according to this example.

Example 2

Protein Adsorption as a Function of the Amount of Metal Particles

A uniform layer of silver was deposited on a silicon dioxide substrate. The substrate was immersed in a cleaning solution of 20% sulphuric acid for 10 minutes at room temperature, followed by rinsing in demineralised water. The surface of the substrate was activated by immersion in an aqueous solution of stannous chloride and the rinsed in demineralised water. The surface of the substrate was then plated with a uniform layer of silver by immersion in 4 baths of deposition solutions comprising silver ions. This yielded a silver surface with an applied amount of 0.8 µg/cm$^2$ corresponding to a thickness of about 77 Å. Particles consisting of 95% palladium and 5% gold were subsequently deposited on the first silver surface by immersion in a dilute suspension of Pd/Au-particles. The applied amount of metal particles was 0.05, 0.12, 0.48 and 0.59 µg/cm$^2$ respectively. The substrate was rinsed in demineralised water and dried.

Adsorption of fibrinogen was studied by the QCM-D technique. Fibrinogen is a glycoprotein synthesised in the liver and is found in blood plasma. QCM-D is a quartz crystal microbalance with dissipation monitoring.

The adsorbed amount of fibrinogen as a function of applied metal particles is shown in table 2.

TABLE 2

| Amount of Pd/Au-particles (µg/cm$^2$) | Fibrinogen adsorption (µg/cm$^2$) |
| --- | --- |
| 0.05 | 2.5 |
| 0.12 | 2.8 |
| 0.48 | 1.8 |
| 0.59 | 2.3 |

Example 3

Growth of Bacteria as a Function of the Amount of Metal Particles

Palladium/gold nanoparticles were deposited in different amounts on a silver base layer, following the method outlined in example 1. The particles comprised 95% palladium and 5% gold. The amount of silver in the base layer was kept constant for all samples. Hence the amount of deposited Pd/Au particles was varied. The growth of bacteria as a function of amount of deposited nanoparticles (Pd/Au) was studied using the following method:

Coated samples were placed into universals. Triplicates were included for each test condition 10 ml of artificial urine (AU) containing inoculated *E. coli* (roughly 10$^5$ CFU/ml) was added to each one and they were incubated horizontally with gentle shaking at 37° C. for 4 hours. After 4 hours the universals were removed from incubation. The samples were removed and CFU (colony forming unit) counts were done from each universal by carrying out 10-fold dilutions in sterile distilled water and plating 100 µl onto a third of a nutrient agar plate. These were incubated for 16-24 hours at 37° C. and the colonies counted. The log CFU/ml versus a control was calculated and is shown in Table 3.

TABLE 3

| Amount of nanoparticles (Pd/Au) (µg/cm$^2$) | Log CFU/ml read vs. control |
| --- | --- |
| 0.78 | 6.5 |
| 0.84 | 7.0 |
| 1.03 | 6.0 |
| 1.10 | 6.5 |
| 1.74 | 5.3 |
| 2.35 | 4.9 |
| 2.41 | 4.6 |

Example 4

Microbial Growth for Several Species

Palladium/gold nanoparticles were deposited in different amounts on a silver base layer on a substrate of silicone, following the method outlined in example 1. The particles comprised 95% palladium and 5% gold. The amount of silver in the base layer was kept constant for all samples. The amount of deposited Pd/Au particles was 0.36 µg/cm$^2$. The antimicrobial properties for different bacterial strains were studied.

Species of microorganisms were chosen with the goal to survey a range of common pathogens (clinical isolates) involved in bacteria transmission and nosocomial infections, namely *Escherichia coli* (*E. coli*), *Pseudomonas aeruginosa*, *Enterococcus* spp, *Klebsiella*, and *Candida*.

The Pd/Au coated silicone samples were placed into universals. Triplicates were included for each test condition. 10 ml of artificial urine containing inoculated organisms (roughly $10^5$ CFU/ml) was added to each one and they were incubated horizontally with gentle shaking at 37° C. for 24 hours.

After 24 hours the universals were removed from incubation. The samples were removed, drained on paper towels and then placed into universals containing 20 ml PBS+Tween and sonicated for 1.5 minutes.

CFU counts were done from each universal by carrying out 10-fold dilutions in sterile distilled water and plating 100 μl onto a third of a nutrient agar plate. These were incubated for 16-24 hours at 37° C. and the colonies counted. In table 4 the reduction of bacteria compared to the uncoated silicone sample is shown. The larger the value the greater reduction.

TABLE 4

| | Reduction vs. Control (Log CFU/cm) | | | | |
|---|---|---|---|---|---|
| | E. coli | Pseudomonas | Enterococcus | Klebsiella | Candida |
| Uncoated Silicone | 0.00 | 0.00 | 0.00 | 0.00 | 0.00 |
| Pd/Au particle coated silicone | 1.64 | 2.53 | 3.88 | 1.37 | 2.52 |

Example 5

A net of polyester fabric was first rinsed in a 5% potassium hydroxide solution for 5 min at 30° C. After repeated rinsing in demineralised water the substrate was immersed in an acidified solution of 1 g/l stannous chloride at room temperature for 10 min. After rinsing in demineralised water it was soaked in a plating bath containing 2 g/l copper sulphate, 5 g/l sodium hydroxide, 50 g/l sodium citrate and 0.005 ml/l formaldehyde for 10 min at 35° C. A copper layer of about 200 Å was obtained and after new rinsing in demineralised water the substrate was immersed in a particle suspension comprising 0.05 g/l each of palladium particles and gold particles. The applied amount of metal particles was 0.4 μg/cm$^2$.

Example 6

A substrate of PMMA was cleaned in 5% hydrochloric acid for 2 min and then rinsed in demineralised water before dipping in a solution containing 0.02 g/l of the stannous ion at a pH of 2.5. After rinsing the substrate was immersed in a solution containing 0.005 g/l of silver ions, 0.02 ml/l ammonia, 0.05 g/l potassium hydroxide and 0.0005 ml/l formaldehyde for 5 min at room temperature. This gave a surface with 0.12 μg/cm$^2$ of silver. After rinsing it was immersed in a particle suspension comprising 0.005 g/l palladium and 0.002 g/l gold particles. The applied amount of metal particles was 0.05 μg/cm$^2$.

Example 7

A non-woven polyimide substrate was immersed in a 12% solution of NaOH at 40° C. for 10 min. After repeated rinsing in demineralised water it was immersed in an alcoholic solution containing 0.5 g/l stannous chloride for 5 min at room temperature. After rinsing it was soaked in a copper bath according to example 3. A copper layer of 2 μg/cm$^2$ was obtained. After rinsing it was immersed in a suspension comprising 1% of Pd and 0.2% of gold particles, calculated on the weight of the total suspension. The applied amount of metal particles was 0.6 μg/cm$^2$.

Example 8

A nylon fabric was cleaned in 5% NaOH for 10 min at 40° C. and after rinsing in demineralised water immersed in a solution of 0.6 g/l stannous chloride at pH 2.2 for 15 min at room temperature. After this the surface comprised a silver amount of 0.8 μg/cm$^2$. After a new rinsing it was dipped in a silver bath according to example 2 and then after new rinsing dipped in a suspension comprising 1% Pd and 0.05% Au particles. The applied amount of metal particles was 0.12 μg/cm$^2$.

Example 9

A substrate of aluminium was treated in a solution of 10% nitric acid and 3% hydrofluoric acid at 60° C. for 20 min. After rinsing, the substrate was dipped in an acidified solution of 3 g/l stannous chloride and after renewed rinsing in a silver bath according to example 2. After this step an amount of around 80 Å silver was obtained on the surface. After another rinsing the substrate was immersed in a suspension comprising 1% Pd and 2% Au particles. The applied amount of metal particles was 0.7 μg/cm$^2$.

Example 10

A substrate of PTFE was etched in an aqueous solution of sodium hydroxide for 5 min. After rinsing and drying it was immersed in a solution containing 0.7 g/l stannous chloride for 20 min at room temperature. The substrate was after rinsing dipped in a plating bath containing 0.2 g/l silver nitrate, 0.5 ml/l ammonia and sodium hydroxide to pH 10.5 for 5 min. After this step an amount of around 2.2 μg/cm silver was obtained on the surface. After a new rinse it was immersed in a suspension comprising 3% Pd and 0.1% Au particles for 5 min at room temperature. The applied amount of metal particles was 0.03 μg/cm$^2$.

Example 11

A glass plate was rinsed in 10% sulphuric acid and 1% hydrofluoric acid at room temperature for 15 min. After rinsing it was immersed in a 1% stannous fluoride solution and after a new rinse immersed in a silver bath according to example 2. After this step an amount of around 140 Å silver was obtained on the surface. After renewed rinsing it was dipped in a suspension comprising 1% ruthenium and 2% palladium particles. The applied amount of metal particles was 0.25 μg/cm$^2$.

Example 12

A stainless steel substrate was immersed in a solution of 15% nitric acid and 5% HF at room temperature for 30 min and then rinsed in demineralised water. The process continued following the steps in example 11. The applied amount of metal particles was 0.9 μg/cm$^2$.

Example 13

A titanium rod was cleaned in a solution of 18% nitric acid and 2% HF for 20 min at room temperature. The application of an electron donating surface and the application of metal particles was made as in example 11. The applied amount of metal particles was 0.6 μg/cm².

Example 14

Complement Activation

Detection of Surface Induced Complement Activation with Quartz Crystal Microbalance with Dissipation Monitoring (QCM-D)

The quantification of a foreign body response is indirectly achieved by monitoring the binding of rabbit-anti human antibodies directed to the surface bound complement factor C3b.

Within seconds from introduction to a soft tissue a foreign body is subject to great attention from the complement system. The complement system comprises about 30 different proteins where C3 is the most abundant. After high concentration body fluid proteins (i.e. Albumin, Fibrinogen and Fibronectin) the complement system is one of the first actors on the scene and aims to protect the host from invading bacteria and fungi, but also to alert the immune system about a foreign body entering the system.

Without being bound by any specific scientific theory the inventors assume that when complement factor 3 (C3) binds to an introduced surface it is cleaved by C3 convertase to form soluble C3a, and surface bound C3b. The surface bound C3b will then act as a convertase itself, triggering subsequent cleavage of C3 in a cascade-like fashion. Receptors to C3b is found on erythrocytes, macrophages, monocytes, polymorphonulear leukocytes and B cells, all of which are important in controlling inflammation and wound healing in tissue. The exact mechanisms controlling the binding of C3 to the surface are still much unknown. However, antibodies directed specifically towards C3b can easily be measured in vitro with QCM-D and give quantitative information of a biomaterial's immune response properties. This new methodology show good agreement with all other known methods for the detection of surface bound C3b.

Material and Methods
Preparation of Surfaces

A coating was applied on standard $SiO_2$ QCM-D crystals (QSX 303, Q-Sense Sweden) using the method outlined in example 2.

As model surfaces standard QCM-D crystals sputtered with Au (s), Ti (s) (QSX301 and QSX310 respectively) was used.

Ag (s) and Pd (s) model surfaces were made on standard gold plated QCM-D-D crystals (QSX 301, Q-Sense Sweden) by high vacuum sputtering of approximately 200 Å Palladium and Silver respectively.

Blood Products

We received fresh whole blood from five healthy donors (Sahlgrenska University Hospital, Göteborg, Sweden). The blood was let to clot in room temperature for approximately 4 hours to obtain complement active serum. The serum was then centrifuged at 4000 rpm for 20 min (Hettich Universal 16 R) after which the supernatant was removed and re-centrifuged as above and stored at −70° C.

Detection of surface induced complement activation Serum was diluted 1:5 in Veronal Buffer Saline supplemented with $CaCl_2$ (0, 15 mM) and $MgCl_2$ (0, 5 mM) ($VBS^{++}$), and the adsorption of serum proteins to the modified QCM-D-crystals were monitored for 20 minutes followed by a rinse with buffer for 5 minutes. The rinse was followed by the addition of rabbit-anti-human C3b antibodies diluted 1:20 in $VBS^{++}$ (Sigma). For negative and positive controls, standard gold QCM-D crystals pre-coated with human IgG (1 mg/ml) (Sigma) were used. The negative control was heat inactivated at 56° C. for 30 min prior to measurements.

All experiments were carried out at room temperature in Veronal Buffer Saline with $CaCl_2$ (0, 15 mM) and $MgCl_2$ (0, 5 mM) ($VBS^{++}$) except for negative controls were $VBS^{--}$ were used. All QCM-D measurements were preformed on the apparatus D300 (Q-sense, Sweden).

Results of the QCM-D measurements of complement activation (C3b). The $SiO_2$ surfaces coated as described above had an amound of silver of 0.35-0.61 μg/cm². The amount of gold in the particles was varied according to the table below and the complement activation was measured according to the table.

| Sample | Amount of Au (μg/cm²) | C3b (ng/cm²) |
|---|---|---|
| Sample No 1 | 0.09 | 677 |
| Sample No 2 | 0.41 | 991 |
| Neg control | — | 109 |
| Pos control | — | 1832 |
| Titan (control) | — | 632 |

Example 15

Platelet Adhesion and Soluble Complement Factor C3a Production on Biomaterial Surfaces The consumption of platelets in fresh whole blood exposed to a biomaterial is used to quantify the thrombogenicity of a desired biomaterial. Moreover, the soluble fraction of activated complement factor 3 (C3a) is used to monitor the complement activation from the biomaterial surface.

BACKGROUND

Platelets (or thrombocytes) are small disc-shaped anuclear cell fragments normally present in healthy blood. They play a crucial role in preserving the walls in blood vessels and are recruited to a damaged area and activated to form a plug, preventing hemorrhage and blood loss. Platelets are also known to adhere and become activated on certain biomaterial surfaces, sometimes forming an undesired and potentially hazardous clot.

Soluble C3a is a small protein cleaved off from the complement factor 3 (C3) when this is bound and activated on a bacteria or a foreign body surface. C3a acts as a chemoattractant for polymorphonuclear monocytes and also have anaphylatoxic properties signaling for the release of histamine from mast cells.

Material and Methods
Experimental Chambers

The experimental chamber is briefly constructed of two PMMA rings glued onto a PMMA microscopic slide, constructing two wells. After addition of whole blood, the material to be tested is placed as a lid over the two wells and held in position with a clip. The chamber is then mounted on a disc rotating in 37° C. water for 60 minutes at 22 rpm.

Blood

Blood was drawn from one healthy donor and collected in a 2× heparinized vial containing soluble heparin (Leo Pharma), to give a final concentration of 1.0 IU heparin/ml. The collected blood was then immediately transferred to the experimental chambers.

Platelet Counting

After incubation in the experimental chamber the blood was added EDTA (Fluka) to a final concentration of 4 mM. Platelets were then counted on a Coulter AcT Diff™ (Coulter Corporation) automated cell counter.

C3a Analysis

After platelet counting, the blood was centrifuged at 4600 g for 10 min at +4° C. and the supernatant (plasma) was saved and stored in −70° C. prior to measurements.

Plasma was diluted 1/300 and analysed in a sandwich ELISA which employs the monoclonal 4SD17.3 (Uppsala university, Sweden) as capture antibody. Bound C3a was detected with biotinylated rabbit anti-human C3a (Dako), followed by HRP-conjugated streptavidin (Amersham Biosciences). Zymosan-activated serum, calibrated against a solution of purified C3a, served as a standard.

Results

Blood platelet count and C3a adsorption. The coated objects manufactured following the method outlined I example 2 on glass had a silver surface concentration of about 1.3 ug/cm2

| Sample | Amount of palladium ($\mu g/cm^2$) | Number of platelets ($\times 10^9$) | C3a ($\mu g/ml$) |
|---|---|---|---|
| Uncoated Glass | — | 29 | 681 |
| coating variation 1 | 0 | 170 | 337 |
| coating variation 2 | 0.01 | 190 | 287 |

Blood platelet count and C3a adsorption. The coatings on glass had a silver surface concentration of about 1.3 $\mu g/cm^2$.

| Sample | Amount of gold ($\mu g/cm^2$) | Number of platelets ($\times 10^9$) | C3a ($\mu g/ml$) |
|---|---|---|---|
| Uncoated Glass | — | 29 | 681 |
| Coating variation 3 | 0.01 | 166 | 376 |
| coating variation 4 | 0.01 | 141 | 271 |

Example 16

Measurement of Inflammatory Response

Material

NHSp-2 (Normal human serum pool from Immunologisk institutt, Rikshospitalet, Oslo, Norway), serum from helthy blood donors.

30 cm PDMS (Polydimethylsiloxane) tubes were coated according to the procedure outlined in example 1. PVC tubes 30 cm were used as control.

Setup: 7 types of tubes, untreated and PVC in triplicate (in total 21).

Method:
1) The serum was placed on ice.
2) A zero sample was removed. 750 μl was added directly to a tube with 15 μl EDTA 0.5M. The sample was kept on ice.
3) 750 μl serum was added to each tube.
4) The tubes were attached to a rotor (5 rpm) 37° C. and were incubated for 30 minutes.
5) The serum was removed with a pipette and added to a tube with 15 μl EDTA 0.5M. The samples were placed on ice and analysed with respect to TCC (the soluble terminal C5b-9 complement complex).

TCC was analyzed using a double antibody enzyme immunoassay based on the monoclonal aE11 antibody, highly specific for a neoepitope exposed on activated but not native C9, as catching antibody. The method was originally described in:

Mollnes T E, Lea T, Frøland S S, Harboe M. "Quantification of the terminal complement complex in human plasma by an enzyme-linked immunosorbent assay based on monoclonal antibodies against a neoantigen of the complex", *Scand J Immunol* 22:197-202. 1985.

and later modified in:

Mollnes T E, Redl H, Høgåsen K, Bengtsson A, Garred P. Speilberg L, Lea T, Oppermann M, Götze O, Schlag G. "Complement activation in septic baboons detected by neoepitope specific assays for C3b/iC3b/C3c, C5a and the terminal C5b-9 complement complex (TCC)", *Clin Exp Immunol* 91:295-300. 1993.

Results

Inflammatory response, amount of Ag=1 μg/cm², coated according to the method outlined in example 2 on a PDMS tube.

| Sample No | Amount Pd ($\mu g/cm^2$) | TCC (pg/ml) | IL-8 (pg/ml) |
|---|---|---|---|
| 1 | 0.47 | 5.85 | 1582.13 |
| 2 | 0.70 | 5.16 | 1724.33 |
| 3 | 1.48 | 4.60 | 2136.79 |
| Uncoated PDMS tube | Uncoated | 3.88 | 728.33 |
| Uncoated PVC tube, control | Uncoated | 6.21 | 1750.23 |

Inflammatory response, amount of Ag=1 μg/cm², coated according to the method outlined in example 2 on a PDMS tube.

| Sample No | Amount Au ($\mu g/cm^2$) | TCC (pg/ml) | IL-8 (pg/ml) |
|---|---|---|---|
| 4 | 0.14 | 5.24 | 1652.62 |
| 5 | 0.32 | 6.51 | 1264.40 |
| Uncoated PDMS tube | Uncoated | 3.88 | 728.33 |
| Uncoated PVC tube, control | Uncoated | 6.21 | 1750.23 |

Example 17

In Vitro Method

Primary normal human dermal fibroblasts (NHDF, Karocell Tissue Engineering AB, Stockholm, Sweden), passage 7, were used. The cells were cultured in tissue culture flasks in complete fibroblast medium containing DMEM+GlutaMAX™-1 (Gibco, UK), 10% foetal bovine serum (FBS, Gibco, UK) and 1% Antibiotic-Antimyocotic (Gibco, UK) at 37° C., 5% $CO_2$ and 95% humidity. Ten different coated materials (PDMS) prepared according to the method outlined in example 1 were sterilely punched into discs with a diameter of 15 mm to fit in a 24-well plate. Discs were dipped in sterile PBS (Phosphate buffered saline solution, Gibco, UK) and 1 ml of cell suspension (17000 cells/ml) was dispersed over the disks and in empty PS-wells (polystyrene, Falcon, BD Biosciences, Belgium) and incubated for 24 h and 72 h in triplicates. Medium from all samples were collected, centrifuged at 400 g, 5 min and stored at −70° C. for ELISA (enzyme-linked immunosorbent assay) analyses of cell released factors. Two discs of each material were incubated with complete medium without cells to estimate background values.

Cell Amount

Cell amounts in association with the surfaces and surrounding medium were determined by a NucleoCounter®-system (ChemoMetec A/S, Denmark). Briefly, cells were treated with lysis buffer and stabilizing buffer (provided with the system). Lysed samples were loaded in a NucleoCassette™ precoated with fluorescent propidium iodide that stains the cell nuclei, and were then quantified in the Nucleo-Counter®.

Cell Viability

Cell viability was determined by measuring lactate dehydrogenase content (LDH) in medium, a marker of cell membrane injury, using a spectrophotometric evaluation of LDH mediated conversion of pyruvic acid to lactic acid (C-Laboratory, Sahlgrenska University Hospital, Göteborg, Sweden).

Cytokine Determination

The amount of TGF-β1 (Transforming Growth Factor beta 1) and type I collagen were detected by ELISA kits (Human TGF-β1, Quantikine®, R&D Systems, UK; Human collagen type1 ELISA KIT, Cosmo Bio Co., Japan) according to the manufacturer's instruction, in a SpectraVmax ELISA reader (Molecular Devices, UK).

In Vivo Method

Six different coated PDMS objects (10 mm in diameter) were coated according to the method outlined in example 1 and were sterilized. Female Spraque-Dawley rats (200-250 g), fed on a standard pellet diet and water were anaesthetized with a mixture of 2.7% isofluran and air (Univentor 400 Anaesthesia Unit, Univentor, Malta) and 0.01 mg Temgesic was given as analgesic s.c. pre-operatively. Rats were shaved and cleaned with 5 mg/ml chlorohexidine in 70% ethanol and each rat received one of each implant type subcutaneously (s.c.) on the back. The wounds were closed with 2 sutures (Ethilon 5-0 FS-3, Ethicon®, Johnson & Johnson, Belgium). The implantation periods were 1 and 3 days to evaluate the early inflammatory process and 21 days for the examination of the fibrous capsule formation and the late inflammatory response (n=8 rats per time period). When the explantation was performed the animals were sacrificed by an overdose of pentobarbital (60 gL$^{-1}$) after short anaesthetics with a mixture of 2.7% isofluran and air. The implants and the surrounding exudates were retrieved. The exudate cells were obtained from the pockets by repeated aspiration of HBSS (Hank's balanced salt solution, Gibco, UK) and kept on ice. The exudates were centrifuged at 400 g, 5 min and supernatants were kept at −70° C. All implantation studies were approved by the Local Ethical Committee for Laboratory Animals.

Cell Amount and Cell Type

The concentration and type of cells in the exudates (cells/ml) were counted by light microscopy with Turk staining in a Bürker chamber and cell amount in centrifuged exudates and on implants were determined by NucleoCounter®-system.

Cell Viability

Cell viability was determined by Trypan Blue exclusion using light microscopy and by LDH evaluation (C-Laboratory, Sahlgrenska University Hospital, Göteborg, Sweden).

Cytokine Determination

The amount of TGF-β1 (Transforming Growth Factor beta 1) and MCP-1 (Monocyte Chemoattractant Protein-1) were detected by ELISA kits (Rat TGF-β1, Quantikine®, R&D Systems, UK; Amersham Monocyte Chemoattractant Protein-1 [(r)MCP-1], Rat, Biotrak ELISA System, GE Healthcare, UK) according to the manufacturer's instruction, in a SpectraVmax ELISA reader (Molecular Devices, UK).

Results from the In Vitro Study

The amount of metals on the test object of PDMS coated according to the method outlined in example 2 was Ag=0.8-0.9 μg/cm$^2$ and Pd=0.1 μg/cm$^2$.

| Surface concentration of Au (μg/cm$^2$) | Number of cells after 72 h |
| --- | --- |
| 0.05 | 5500 |
| 0.34 | 9400 |
| 0.43 | 16200 |

In the second experimental set the amount of metals on the test object of PDMS coated according to the method outlined in example 2 was Ag=0.8-0.9 μg/cm$^2$ and Au=0.05-0.09 μg/cm$^2$.

| Surface concentration of Pd (μg/cm$^2$) | Number of cells after 72 h |
| --- | --- |
| 0.1 | 5500 |
| 0.27 | 8600 |
| 0.69 | 9900 |

Results from the In Vivo Study

The Amount of Pd was varied on PDMS discs in vivo. The amount of Ag was about 1 μg/cm$^2$ for all samples. (PMN=polymorphonuclear)

| Amount of Pd (μg/cm$^2$) | % PMN cells in exudate, 1 day | % PMN cells in exudate, 3 days | % PMN cells in exudate, 21 days |
| --- | --- | --- | --- |
| Uncoated PDMS control | 33 | 2 | 1 |
| 0 | 17 | 2 | 1 |
| 0.07 | 32 | 2.5 | Below 1 |
| 0.86 | 26 | 2 | Below 1 |

| Amount of Pd (μg/cm$^2$) | Total amount of MCP-1, 1 day (pg/ml) | Total amount of MCP-1, 3 days (pg/ml) | Total amount of MCP-1, 21 days (pg/ml) |
| --- | --- | --- | --- |
| Uncoated PDMS control | 4600 | 500 | 100 |
| 0 | 2050 | 700 | 350 |
| 0.07 | 4500 | 500 | 200 |
| 0.86 | 3300 | 600 | 200 |

| Amount of Pd (μg/cm²) | Total amount of TGF-1, 1 day (pg/ml) | Total amount of TGF-1, 3 days (pg/ml) | Total amount of TGF-1, 21 days (pg/ml) |
|---|---|---|---|
| Uncoated PDMS control | 62 | 1 | 10 |
| 0 | 3 | 8 | 12 |
| 0.07 | 82 | 33 | 11 |
| 0.86 | 25 | 8 | 20 |

The Amount of Au was varied on discs in vivo. The amount of Ag was about 1 μg/cm² for all samples. (PMN=polymorphonuclear)

| Amount of Au (μg/cm²) | % PMN cells in exudate, 1 day | % PMN cells in exudate, 3 days | % PMN cells in exudate, 21 days |
|---|---|---|---|
| Uncoated PDMS control | 33 | 2 | 1 |
| 0.01 | 32 | 2.5 | 1 |
| 0.43 | 18 | 5 | 1.5 |
| 0.64 | 20 | 4 | Below 1 |

| Amount of Au (μg/cm²) | Total amount of MCP-1, 1 day (pg/ml) | Total amount of MCP-1, 3 days (pg/ml) | Total amount of MCP-1, 21 days (pg/ml) |
|---|---|---|---|
| Uncoated PDMS control | 4600 | 500 | 100 |
| 0.01 | 4500 | 500 | 200 |
| 0.43 | 3100 | 450 | 200 |
| 0.64 | 2800 | 500 | 150 |

| Amount of Au (μg/cm²) | Total amount of TGF-1, 1 day (pg/ml) | Total amount of TGF-1, 3 days (pg/ml) | Total amount of TGF-1, 21 days (pg/ml) |
|---|---|---|---|
| Uncoated PDMS control | 62 | 1 | 10 |
| 0.01 | 82 | 33 | 11 |
| 0.43 | 6 | 5 | 20 |
| 0.64 | 28 | 8 | 9 |

Below are described a number of specific uses of the coating according to the present invention.

Contact Lenses

Contact lenses are often made of a polymeric material with significant water content. It is essential to avoid microbial growth on a contact lens. By using the method outlined above it is possible to coat a contact lens to prevent or reduce microbial growth. A coated contact lens will also be biocompatible. In the examples above it has been demonstrated that polymeric material can be coated according to the invention. As examples of coating of polymeric substrates can be mentioned coating of polyester (example 5), PMMA (example 6), polyimide (example 7), nylon (example 8), and PTFE (example 9). The fact that the coating successfully can be applied to those polymeric materials shows that the coating also can be applied to contact lenses of polymeric materials.

Pacemakers, and Pacemaker Electrodes

Pacemakers to be inserted into the body of a human have to be biocompatible. At the same time it is desirable if they prevent microbial growth. A pacemaker or pacemaker electrode coated with the present coating has those desirable properties. Above it has been shown that the coating can be applied to many materials, for instance metals such as titanium (example 13), stainless steel (example 12), and aluminium (example 9). Thus a pacemaker or pacemaker electrode made of metal or any other material can successfully be coated according to the present invention.

Stents (Bare Metal and Drug Eluting)

Stents to be inserted into the body of a human should preferably be biocompatible. At the same time it is desirable if they prevent microbial growth. A stent coated with the present coating has those desirable properties. Above it has been shown that the coating can be applied to metals such as titanium (example 13), stainless steel (example 12), and aluminium (example 9). Stents may be manufactured of these and other metals or alloys and may successfully be coated with the coating according to the present inventions.

Dental Implants

Dental implants are advantageously both biocompatible and antimicrobial. Dental implants can be made of titanium or any other materials. As shown above in example 13, titanium can be coated according to the present invention. A dental implant coated according to the present invention is both biocompatible and antimicrobial. One example of a dental implant is a dental implant made of titanium and coated as described in example 13.

Rupture Nets, Mesh

Materials for nets and meshes can be coated as shown for polyester (example 5), PMMA, (example 6), polyimide (example 7), and nylon (example 8). Such nets and meshs will be both antimicrobial and biocompatible which is an advantages within many applications.

Blood Centrifuge Equipment (in Contact with Blood)

In equipment intended for contact with blood the biocompatible and antimicrobial properties of the coating according to the present invention are desired. Materials in contact with blood can be selected from a large number of materials. In the examples above we have shown that a large variety of materials can be coated, such as glass (example 1, 2, 4, and 11), polyester (example 5), PMMA, (example 6), polyimide (example 7), nylon (example 8), aluminium (example 9), PTFE (example 10), stainless steel (example 10), and titanium (example 13). Blood centrifuge equipment comprising a substrate coated according to the present invention has improved properties regarding biocompatibility and antimicrobial properties.

Surgical Instruments

It is highly desirable that surgical instruments display antimicrobial properties. Materials often used for surgical instruments such as stainless steel and titanium can be coated as shown in examples 12 and 13 respectively. By using the coating according to the present invention the desired antimicrobial properties are achieved. Moreover the coating is also biocompatible.

Gloves

It is often desired that gloves used for various purposes display antimicrobial properties. Moreover gloves which at the same time are tissue friendly and biocompatible are desired for some applications. By coating gloves with the coating according to the present invention the above mentioned desired properties are achieved. Polymeric materials can be coated according to the present invention with excellent results and examples of several polymeric materials are given above.

Blood Bags

In blood bags intended for contact with blood the biocompatible and antimicrobial properties of the coating according to the present invention are desired. Materials for blood bags are most often polymeric materials. Polymeric materials can be coated according to the present invention with excellent results and examples of several polymeric materials are given above.

Artificial Heart Valves

For artificial heart valves the antimicrobial and biocompatible properties of the coating according to the present invention are highly desired. The coating can be applied successfully both to polymeric materials and metals that may constitute an artificial heart valve. The above mentioned examples show that the coating can be applied to both polymeric materials and metals as well as alloys.

Central Venous Catheters

For catheters to be inserted into the body such as central venous catheters, antimicrobial properties are highly desired. Moreover objects to be inserted into the human body also should be biocompatible and tissue friendly. The coating according the present invention fulfils the requirements and has excellent properties for catheters. Materials used for catheters can be coated successfully with the coating according to the present invention.

Peripheral Venous Catheters

Regarding antimicrobial and biocompatible properties the requirements for peripheral venous catheters and central venous catheters are similar. Thus the coating according to the present invention is also excellent for peripheral venous catheters.

Vascular Ports

Regarding vascular ports there is an infection risk and moreover such vascular ports should be biocompatible. Therefore the coating according to the present invention is excellent for vascular ports so that they become antimicrobial and biocompatible. Materials used for vascular ports can successfully be coated with the coating according to the present invention.

Haemodialysis Equipment

For haemodialysis equipment antimicrobial and biocompatible properties are important, thus making the coating according to the present invention very suitable.

Peritoneal Dialysis Equipment

For peritoneal dialysis equipment the antimicrobial and biocompatible properties of the coating according to the present invention are very useful. It is suitable to apply the coating according to the present invention to parts of such equipment.

Plasmapheresis Devices

For plasmapheresis devices, including catheters implanted for such purpose, the coating according to the present invention is suitable due to its antimicrobial and biocompatible properties. Materials used in this context can successfully be coated according to the present invention.

Inhalation Drug Delivery Devices

Inhalation drug delivery devices advantageously display antimicrobial properties which is achieved by coating suitable parts of the device with the coating according to the present invention. The biocompatible properties of the coating is also an advantage.

Vascular Grafts (for Example Arterial Grafts)

Vascular grafts benefit from antimicrobial and biocompatible properties, which are achieved by the coating according to the present invention. The materials which the grafts are made of are suitable for coating according to the present invention.

Cardiac Assist Devices

Cardiac assist devices to be implanted into the body should be both biocompatible and antimicrobial. This is achieved by using a coating according to the present invention. Materials used for such devices are successfully coated using the present invention.

Wound Dressings

Wound dressings are preferably antimicrobial as well as biocompatible. This make them excellent objects for coating according to the present invention. Polymeric and fibrous material used for wound dressings are successfully coated according to the present invention.

Intermittent Catheters

Intermittent catheters as well as other catheters should preferably be both antimicrobial to avoid problems with infections, moreover they should also be biocompatible. The coating according to the present invention is excellent for catheters since it is both antimicrobial and biocompatible. Materials used for catheters can successfully be coated according to the present invention.

ECG Electrodes

ECG electrodes should preferably be both antimicrobial and biocompatible. ECG electrodes coated according to the present invention are both antimicrobial and biocompatible. Materials such as titanium (example 13), stainless steel (example 12), and aluminium (example 9) can as well as many other materials suitable for electrodes be coated according to the present invention.

Peripheral Stents

Desired properties for peripheral stents are similar to those for stents as described above. Thus also peripheral stents can successfully be coated according to the present invention.

Bone Replacing Implants

Implants of different kinds such as bone replacing implants are preferably both antimicrobial and biocompatible. This is achieved by a coating according to the present invention.

Orthopaedic Implants

Orthopaedic implants as are very suitable to coat according to the present invention to render them antimicrobial and biocompatible. Examples of orthopaedic implants include hip replacements, total hip replacements, ceramic hip replacements, hip joint replacements, knee replacements, total knee replacements, and knee joint replacements.

Orthopaedic Devices (Screws, Pins, Staples, Suture Anchors Etc)

All kinds of orthopaedic devices such as screws, pins, staples, and suture anchors are preferably both antimicrobial and biocompatible. Such devices are made of materials which successfully can be coated according to the present invention. Orthopaedic devices benefit from coating according to the present invention. One example of an orthopaedic device a screw of titanium coated according to the procedure described in example 13.

Tissue Replacing Implants

Implants of different kinds such as tissue replacing implants are advantageously both antimicrobial and biocompatible. This is achieved by a coating according to the present invention on the tissue replacing implants.

Intraocular Lenses

For intraocular lenses it is an advantage if they are antimicrobial and biocompatible. This is achieved by coating according to the present invention. Intraocular lenses made of polymeric materials and other materials can successfully be coated according to the present invention.

Sutures

It is a great advantage for sutures to be antimicrobial and biocompatible. Sutures are therefore suitable for coating according to the present invention.

Needles

Needles that should be antimicrobial and/or biocompatible can successfully be coated according to the present invention to give the desired antimicrobial and biocompatible properties.

Drug Delivery Devices

Drug delivery devices which shall be made antimicrobial and/or biocompatible are advantageously coated according to the present invention.

Endotracheal Tubes

Endotracheal tubes are preferably antimicrobial as well as biocompatible. The polymeric materials that are used to manufacture endotracheal tubes are suitable for coating according to the present invention. Thus endotracheal tubes can successfully be coated according to the present invention to give the desired antimicrobial and biocompatible properties.

Shunts

For various kinds of shunts it is highly desirable that they display antimicrobial properties and that they are biocompatible. The materials that are used for shunts can successfully be coated according to the present invention and thus the shunt will get the desired properties.

Drains

Drains are preferably antimicrobial and also biocompatible. Since the coating according to the present invention successfully can be applied to the materials from which drains are made, it is very suitable to apply the coating according to the present invention to drains.

Suction Devices

Suction devices should be antimicrobial and also biocompatible. Since the coating according to the present invention successfully can be applied to the materials from which suction devices are made, it is very desirable to apply the coating according to the present invention to suction devices.

Hearing Aid Devices

Hearing aid devices are preferably antimicrobial and also biocompatible. The materials that hearing aid devices are made from can successfully be coated according to the present invention. Hearing aid devices are very suitable to coat according to the present invention.

Urethral medical devices such as catheters, urethral stents and suprapubic stents are suitable to coat according to the present invention.

Artificial blood vessels are suitable to coat according to the present invention.

What is claimed is:

1. A device comprising a substrate having an electron donating surface, wherein said electron donating surface comprises a metal selected from the group consisting of silver and zinc, wherein metal particles are deposited on said electron donating surface, said metal particles comprising palladium and at least one metal selected from the group consisting of gold, ruthenium, rhodium, osmium, iridium, and platinum and wherein the amount of said metal particles is from 0.001 to about 8 µg/cm$^2$, and wherein the metal particles do not form a covering layer, but are uniformly distributed particles or clusters on said electron donating surface.

2. The device according to claim 1, wherein said silver in said electron donating surface is present in an amount of about 0.05 to about 12 µg/cm$^2$.

3. The device according to claim 1, wherein said substrate is a polymeric substrate.

4. The device according to claim 3, wherein said polymeric substrate is selected from the group consisting of latex, vinyl, polymers comprising vinyl groups, polyurethane urea, silicone, polyvinylchloride, polypropylene, styrene, polyurethane, polyester, copolymerisates of ethylene vinyl acetate, polystyrene, polycarbonate, polyethylene, polyacrylate, polymethacrylate, acrylonitrile butadiene styrene, polyamide, and polyimide, or mixtures thereof.

5. The device according to claim 1, wherein said substrate is formed from a metal.

6. The device according to claim 5, wherein said metal of said substrate is selected from the group consisting of stainless steel, medical grade steel, titanium, medical grade titanium, cobalt, and chromium or mixtures thereof.

7. The device according to claim 1, wherein said substrate is selected from the group consisting of glass, minerals, zeolites, stone and ceramics.

8. The device according to claim 1, wherein said substrate is selected from the group consisting of paper, wood, woven fibres, fibres, cellulose fibres, leather, carbon, carbon fibres, graphite, polytetrafluoroethylene, and polyparaphenyleneterephthalamide.

9. The device according to claim 1, wherein the amount of the metal particles of the metal deposited onto said metal electron donating surface is from about 0.01 to about 4 µg/cm$^2$.

10. The device according to claim 1, wherein the ratio of palladium to non-palladium metals in said metal particles is from about 0.01:99.99 to about 99.99:0.01.

11. The device according to claim 1, wherein the ratio of palladium to non-palladium metals in said metal particles is from about 0.5:99.5 to about 99.8:0.2.

12. The device according to claim 1, wherein the ratio of palladium to non-palladium metals in said metal particles is from about 2:98 to about 95:5.

13. The device according to claim 1 wherein said metal particles, comprise palladium and gold.

14. The device according to claim 1, wherein said metal particles have an average size of about 10-10000 Å.

15. The device according to claim 1, wherein said metal particles have an average size of about 100-600 Å.

16. The device according to claim 1, wherein said device is a contact lens.

17. The device according to claim 1, wherein said device is a pacemaker.

18. The device according to claim 1, wherein said device is a stent.

19. The device according to claim 1, wherein said device is a dental implant.

20. The device according to claim 1, wherein said device is a rupture net.

21. The device according to claim 1, wherein said device is a blood centrifuge equipment.

22. The device according to claim 1, wherein said device is a surgical instrument.

23. The device according to claim 1, wherein said device is a glove.

24. The device according to claim 1, wherein said device is a blood bag.

25. The device according to claim 1, wherein said device is an artificial blood valve.

26. The device according to claim 1, wherein said device is a central venous catheter.

27. The device according to claim 1, wherein said device is a peripheral venous catheter.

28. The device according to claim 1, wherein said device is a vascular port.

29. The device according to claim 1, wherein said device is a haemodialysis equipment.

30. The device according to claim 1, wherein said device is a peritoneal dialysis equipment.

31. The device according to claim 1, wherein said device is a plasmapheresis device.

32. The device according to claim 1, wherein said device is an inhalation drug delivery device.

33. The device according to claim 1, wherein said device is a vascular graft.

34. The device according to claim 1, wherein said device is a cardiac assist device.

35. The device according to claim 1, wherein said device is a wound dressing.

36. The device according to claim 1, wherein said device is an intermittent catheter.

37. The device according to claim 1, wherein said device is an ECG electrode.

38. The device according to claim 1, wherein said device is a peripheral stent.

39. The device according to claim 1, wherein said device is a bone replacing implant.

40. The device according to claim 1, wherein said device is an orthopaedic implant.

41. The device according to claim 1, wherein said device is an orthopaedic device.

42. The device according to claim 1, wherein said device is a tissue replacing implant.

43. The device according to claim 1, wherein said device is an interocular lens.

44. The device according to claim 1, wherein said device is a suture.

45. The device according to claim 1, wherein said device is a needle.

46. The device according to claim 1, wherein said device is a drug delivery device.

47. The device according to claim 1, wherein said device is an endotracheal tube.

48. The device according to claim 1, wherein said device is a shunt.

49. The device according to claim 1, wherein said device is a drain.

50. The device according to claim 1, wherein said device is a suction device.

51. The device according to claim 1, wherein said device is a hearing aid device.

52. The device according to claim 1, wherein said device is an urethral medical device.

53. The device according to claim 1, wherein said device is an artificial blood vessel.

54. Use of a device according to claim 1 for modifying protein adsorption to said device, comprising the step of contacting, said device with at least one protein.

55. Use of a device according to claim 1 for modifying bacterial adhesion to said device, comprising the step of contacting said device with bacteria.

56. Use of a device according to claim 1 for modifying tissue ingrowth on said device, comprising the step of contacting said device with growing tissue.

57. Use of a device according to claim 1 for modifying complement activation caused by said device, comprising contacting said device with at least a part of molecules belonging to a complement system.

58. Use of a device according to claim 1 for modifying inflammatory response caused by said device, comprising contacting said device with at least one type of cells in a living organism.

59. Use of a device according to claim 1 for modifying blood clotting caused by said device, comprising contacting said device with blood.

60. Use of a device according to claim 1 for preventing bacterial growth, comprising placing said device in an environment with risk for bacterial growth.

61. Use of a device according to claim 1 for preventing transmission of bacteria, comprising using said device in a situation with risk of transmission of bacteria.

62. Use of a device according to claim 1 for preventing nosocomial infections, comprising using said device in a hospital environment.

63. Use of a device according to claim 1 for modifying the friction coefficient of said device, comprising using said device in a way where the friction coefficient needs to be modified.

64. Use of a device according to claim 1 for modifying the surface hardness of said device, comprising using said device in a way where the surface hardness needs to be modified.

65. A method for the manufacture of a device comprising a substrate according to claim 1 said method comprising the steps:
   a. depositing metal particles from a suspension onto said substrate,
   b. rinsing said substrate, and
   c. drying said substrate.

66. The method according to claim 65 further comprising the step of depositing an electron donating material on said substrate before the deposition of metal particles.

* * * * *